US008816308B2

(12) United States Patent
Tanaka

(10) Patent No.: US 8,816,308 B2
(45) Date of Patent: Aug. 26, 2014

(54) RI MANUFACTURING APPARATUS

(75) Inventor: Hideki Tanaka, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 20 days.

(21) Appl. No.: 13/409,339

(22) Filed: Mar. 1, 2012

(65) Prior Publication Data

US 2012/0223254 A1 Sep. 6, 2012

(30) Foreign Application Priority Data

Mar. 2, 2011 (JP) ................................ 2011-045283

(51) Int. Cl.
*A61N 5/00* (2006.01)
*G21G 1/00* (2006.01)

(52) U.S. Cl.
USPC ................. 250/505.1; 250/492.21; 250/492.3

(58) Field of Classification Search
CPC .................................. G21G 1/00; A61N 5/00
USPC ...................................................... 250/505.1
See application file for complete search history.

(56) References Cited

U.S. PATENT DOCUMENTS

| | | | | |
|---|---|---|---|---|
| 7,394,081 | B2 * | 7/2008 | Okazaki et al. | 250/492.3 |
| 8,374,306 | B2 * | 2/2013 | Norling et al. | 376/190 |

FOREIGN PATENT DOCUMENTS

| | | | |
|---|---|---|---|
| JP | 2005-127901 | A | 5/2005 |
| JP | 2007095553 | A | 4/2007 |
| JP | 20100223944 | A | 10/2010 |
| JP | 2011033468 | A | 2/2011 |
| WO | 2010/129157 | A1 | 11/2010 |

OTHER PUBLICATIONS

Office Action dated Sep. 10, 2013, issued in corresponding JP2011-045283.
Japanese Office Action dated Jun. 3, 2014, for corresponding Japanese Patent Application No. P2011-045283.

* cited by examiner

*Primary Examiner* — Philip A Johnston
(74) *Attorney, Agent, or Firm* — Squire Patton Boggs (US) LLP

(57) ABSTRACT

An RI manufacturing apparatus includes: an accelerator which accelerates charged particles; a target which is irradiated with the charged particle accelerated by the accelerator, thereby manufacturing a radioactive isotope; a built-in shield that may be a wall body which surrounds the accelerator and the target to shield radiation; and a target shield that may be a wall body which is disposed between the built-in shield and the accelerator and surrounds the target to shield the radiation.

4 Claims, 6 Drawing Sheets

RI MANUFACTURING APPARATUS

RELATED APPLICATION

Priority is claimed to Japanese Patent Application No. 2011-045283, filed Mar. 2, 2011, the entire content of which is incorporated herein by reference.

BACKGROUND

1. Technical Field

The present invention relates to an RI (radioactive isotope) manufacturing apparatus.

2. Description of the Related Art

In the manufacturing of a medicine for examination labeled with a radioactive element which is used for positron emission tomography (PET), for example, or radiation therapy, a particle accelerator such as a cyclotron is used. At the time of an operation of the particle accelerator, since radiation such as neutron radiation or gamma rays is generated, it is necessary shield the radiation.

In the past, shielding of the radiation has been performed by covering a building itself in which the particle accelerator is installed, by a radiation shielding wall body. However, in recent years, from the viewpoint of reducing the weight and cost of the building, a so-called self-shielding type particle accelerator system has been developed in which the particle accelerator itself is surrounded and shielded by a radiation shielding wall body (refer to the related art, for example).

In an accelerator system described in the related art, a built-in shield (a radiation shielding wall body) which surrounds a particle accelerator itself is configured so as to be formed divided into a fixed-side radiation shielding wall body and a movable-side radiation shielding wall body and be able to open the inside by moving the movable-side radiation shielding wall body. For example, when performing maintenance of the cyclotron that is an accelerator, it becomes possible to easily access the inside by opening the inside by moving a movable-side block.

SUMMARY

According to an embodiment of the present invention, there is provided an RI manufacturing apparatus includes: an accelerator which accelerates charged particles; a target which is irradiated with the charged particle accelerated by the accelerator, thereby manufacturing a radioactive isotope; a built-in shield that is a wall body which surrounds the accelerator and the target to shield radiation; and a target shield that is a wall body which is disposed between the built-in shield and the accelerator and surrounds the target to shield the radiation.

DETAILED DESCRIPTION

Figure 1:
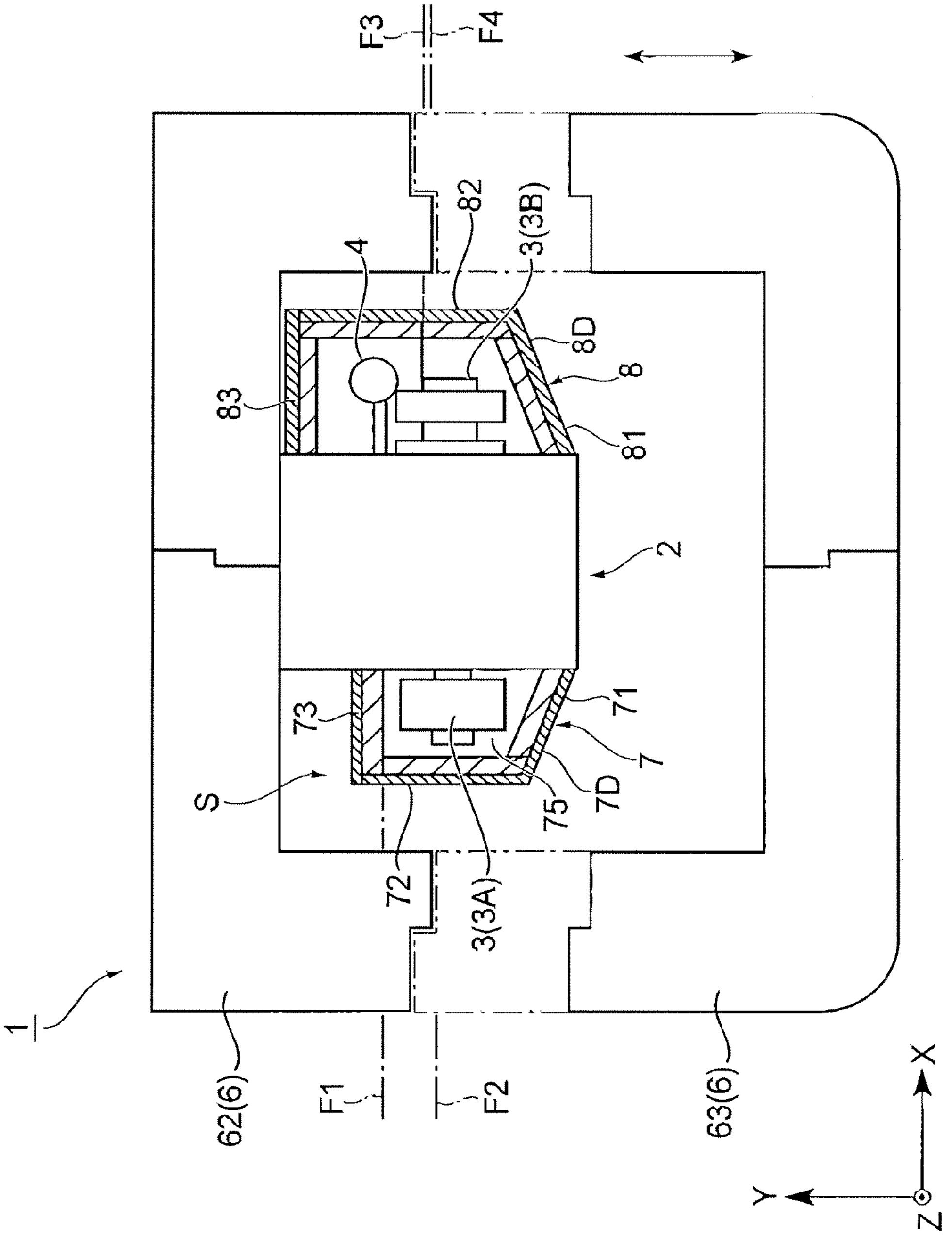
FIG. 1 is a cross-sectional view along the X-Y plane of an RI manufacturing apparatus according to an embodiment of the present invention.

Since a target of an RI manufacturing apparatus which manufactures an RI is directly exposed to a charged particle beam, activation proceeds by a day-to-day operation. If activation proceeds, since radiation is radiated from the target even after shutdown (after the stopping of irradiation of the charged particle beam), during the maintenance of equipment other than the target provided inside the built-in shield, it is necessary to open the built-in shield after waiting for attenuation of the radiation. For this reason, there is a problem of a longer shutdown time.

It is desirable to provide an RI manufacturing apparatus in which during the maintenance of equipment disposed in a built-in shield, it is possible to reduce the fear of exposure from an activated target and it is possible to shorten the waiting time for attenuation of radiation.

According to the RI manufacturing apparatus configured in this manner, because of a configuration in which the target shield that may be a wall body which surrounds the target to shield the radiation is provided further to the inside than the built-in shield, it is possible to shield the radiation which is radiated from an activated target. For this reason, even if the built-in shield is opened, since the radiation from the target is shielded by the target shield, when performing maintenance of equipment other than the target disposed further to the inside than the built-in shield, it is possible to perform work without waiting for attenuation of the radiation and it is possible to reduce the fear of exposure of a worker. Further, because of a configuration in which the target shield is provided further to the inside than the built-in shield, the built-in shield disposed further to the outside than the target shield produces the same shielding effects as in the past by using a smaller amount of shielding material than in the past.

Here, the target shield may include a gamma ray shielding plate which shields gamma rays, and a neutron radiation shielding plate which is disposed on the target side of the gamma ray shielding plate and shields neutron radiation. In this manner, in the case of a configuration in which the neutron radiation shielding plate is provided on the target side and the gamma ray shielding plate is provided on the outer side of the neutron radiation shielding plate, it is possible to shield the gamma rays which are generated by hitting of the neutron radiation against the neutron radiation shielding plate, by the outer gamma ray shielding plate.

Further, the built-in shield may be composed of a plurality of parts, at least one of the plural parts may be configured to be movable, the target shield may have an openable and closable door, and a joint between the door and a member adjacent to the door may be formed at a position deviated from a joint between the plural parts of the built-in shield. In this manner, if the door is provided in the target shield, when performing maintenance of the target disposed inside, since it is possible to easily access the target by opening the door, it becomes possible to facilitate maintenance work such as replacement work of the target. Further, by disposing the joint of the door of the target shield and the joint of the outer built-in shield at positions being out of alignment, disposition of both the joints on the same straight line is avoided, so that it is possible to reduce the fear of transmission of the radiation through the joints.

Further, a cutout portion which makes a lead-out tube that leads out the radioactive isotopes in the target pass therethrough may be provided on the lower surface side of the target shield. The radioactive isotopes which are accommodated in the target pass through the lead-out tube and are led out to the outside of the RI manufacturing apparatus. At this time, if the cutout portion which passes the lead-out tube therethrough is provided on the bottom face side of the target where the need to shield the radiation is small, the radiation passed the cutout portion are attenuated by being hit on and reflected by a floor surface, and a distance increases due to the reflection, so that attenuation due to the distance becomes large, whereby the fear of exposure of a worker is reduced. Further, since there is also no need for a worker to enter beneath the target shield during maintenance, so that it is also not necessary to take into account exposure by the radiation advancing downward, even in a case where a radiation shielding wall body covering the bottom face side of the target is not present, it does not particularly matter, In this manner, according to an embodiment of the present invention, since the target shield which surrounds the target to shield the radiation is provided, even in a case where the built-in shield is opened, it is possible to reduce the fear of exposure from an activated target, and during the maintenance of equipment other than the target disposed in the built-in shield, it is possible to shorten the waiting time for attenuation of the radiation, so that it is possible to shorten a shutdown time.

Hereinafter, an RI manufacturing apparatus according to an embodiment of the present invention will be described referring to FIGS. 1 to 6. In addition, in the description of the drawings, the same or equivalent element is denoted by the same reference numeral and overlapping description will be omitted. Further, positional relationships such as up-and-down and left-and-right are set to be based on positional relationships in the drawings.

RI Manufacturing Apparatus

FIG. 1 is a cross-sectional view of an RI manufacturing apparatus according to an embodiment of the present invention. An RI manufacturing apparatus 1 according to this embodiment is for manufacturing a radioactive isotope (RI). The RI manufacturing apparatus 1 can be used as a cyclotron for PET, for example, and the RI manufactured by the RI manufacturing apparatus 1 is used for the manufacturing of a radioactive drug (including radioactive medicines) that is a radioactive isotope-labeled compound (an RI compound), for example. As the radioactive isotope-labeled compound which is used for PET examination (positron emission tomography examination) in a hospital or the like, $^{18}$F-FLT (fluorothymidine), $^{18}$F-FMISO (fluoromisonidazole), $^{11}$C-raclopride, or the like is present.

The RI manufacturing apparatus 1 is a so-called self-shielding type particle accelerator system and includes an accelerator (a cyclotron) 2 which accelerates charged particles and a built-in shield 6 that may be a radiation shield (wall body) which surrounds the accelerator 2 to shield radiation. In an internal space S formed so as to be surrounded by the built-in shield 6, in addition to the accelerator 2, a target 3 which is used to manufacture the RI, a vacuum pump 4 for vacuumizing the inside of the accelerator 2, and the like are disposed. Further, in the internal space, accessories required for an operation of the accelerator 2, a lead-out tube (not shown) for leading the RI in the target 3 out of the apparatus, ancillary equipment which is used for cooling of the target 3, and the like are disposed.

Accelerator

Figure 4:
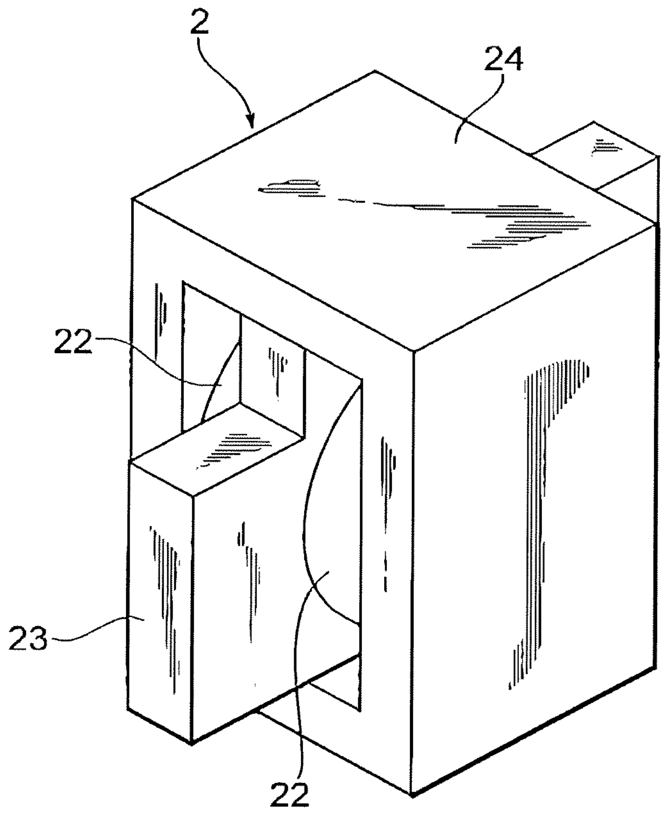
FIG. 4 is a perspective view showing an accelerator of the RI manufacturing apparatus according to the embodiment of the present invention.

The accelerator 2 may be a so-called vertical type cyclotron, as shown in FIG. 4, and includes a pair of magnetic poles 22, a vacuum box 23, and an annular yoke 24 which surrounds the pair of magnetic poles 22 and the vacuum box 23. The upper surfaces of the pair of magnetic poles 22 partially face each other at a predetermined interval in the vacuum box 23. A charged particle such as a hydrogen ion is accelerated multiple times in the gap between the pair of magnetic poles 22. The vacuum pump 4 is used to maintain vacuum environment in the accelerator 2 and fixed to a side portion of the accelerator 2, for example.

Target

Figure 2:
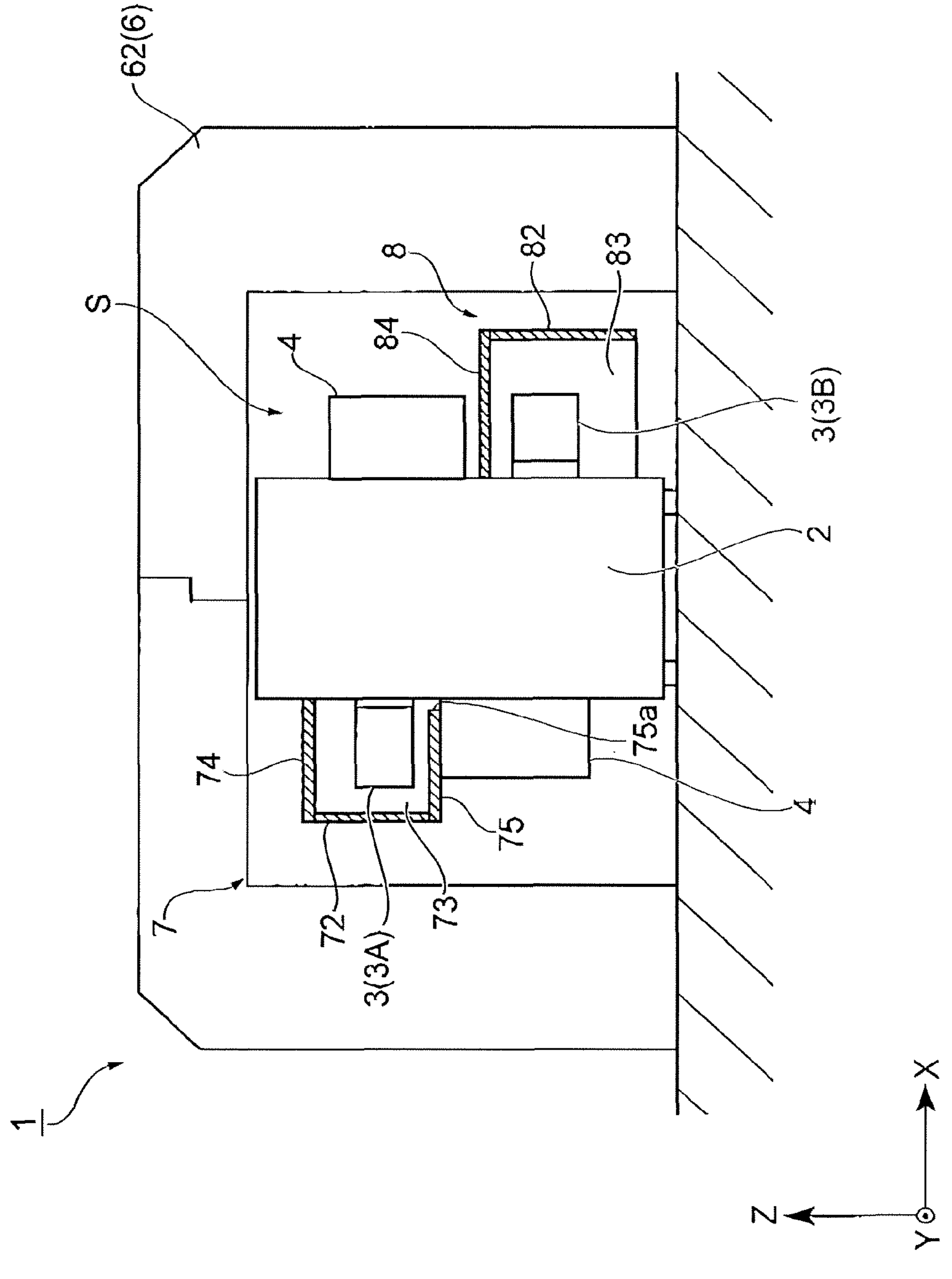
FIG. 2 is a cross-sectional view along the Z-X plane of the RI manufacturing apparatus according to the embodiment of the present invention.

The target 3 is for receiving a charged particle beam irradiated from the accelerator 2, thereby manufacturing the RI, and in the inside thereof, an accommodating portion which accommodates a raw material (for example, target water) is formed. The target 3 is generally fixed to a side portion of the accelerator 2, as shown in FIGS. 1 and 2. The target 3 is a site which is the most exposed to the charged particle beam, is activated during operation, and emits radiation even after shutdown. In the RI manufacturing apparatus 1 according to this embodiment, a plurality of targets 3 is provided. The targets 3 are disposed on both sides in the X direction of the illustration with the accelerator 2 interposed therebetween. For example, the target 3 (3A) disposed in the left side of the illustration is disposed on the upper stage side and the target 3 (3B) disposed in the right side of the illustration is disposed on the lower stage side (refer to FIG. 2). The lead-out tube forms a fluid passage which communicates with and is also connected to the accommodating portions of the targets 3, thereby leading the manufactured RI out of the RI manufacturing apparatus 1.

Built-in Shield

Figure 3:
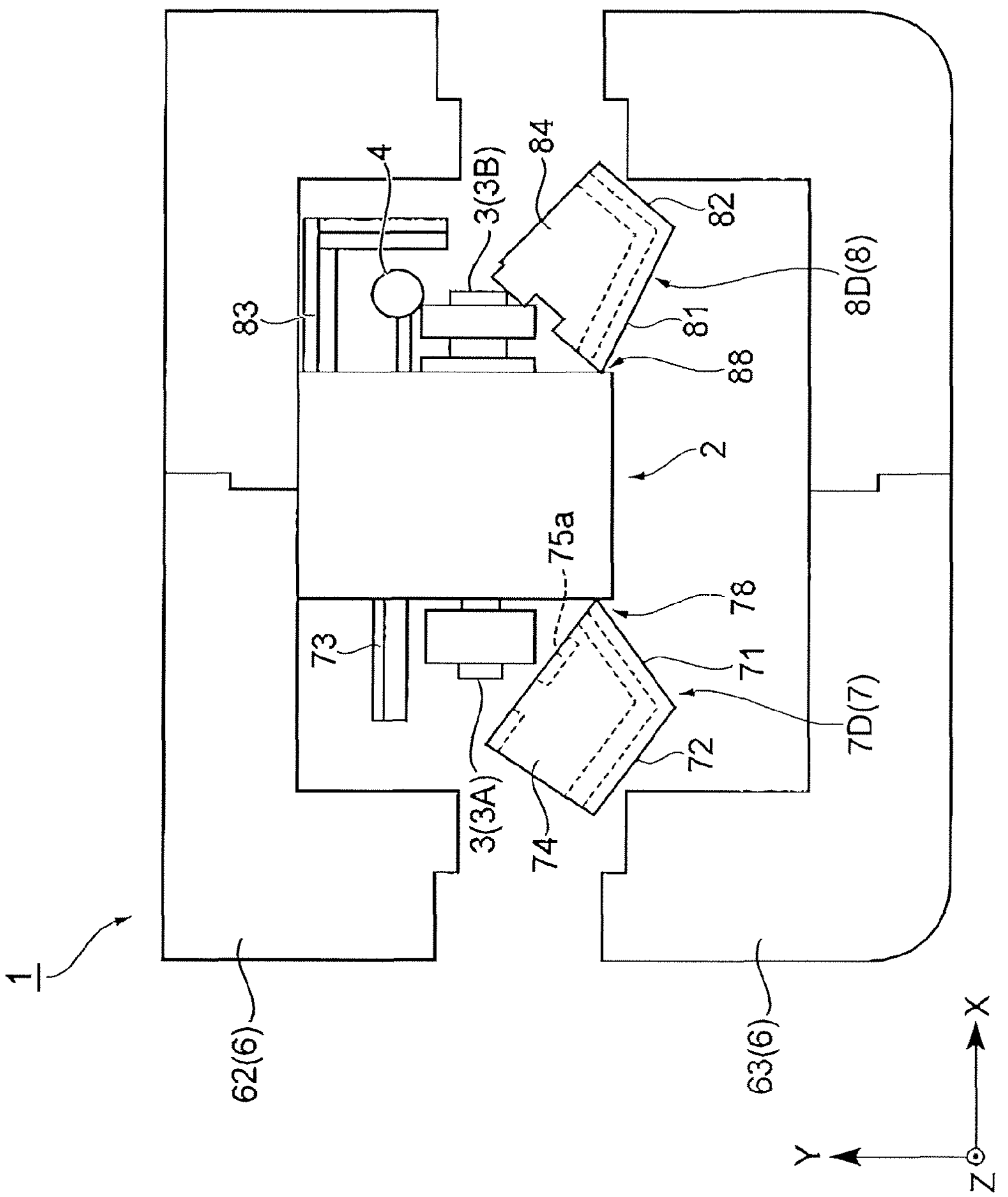
FIG. 3 is a cross-sectional view along the X-Y plane of the RI manufacturing apparatus according to the embodiment of the present invention and is a diagram showing a state where target shields have been opened.

The built-in shield 6 is composed of a plurality of parts, as shown in FIGS. 1 to 3, and includes a rear wall body 62 and a front wall body 63 as the plurality of parts. The rear wall body 62 is disposed so as to cover the back face side of the accelerator 2. The rear wall body 62 is formed, for example, so as to cover the whole of the back face of the accelerator 2, halves on the back face side of both side portions of the accelerator 2, and half on the back face side of the surface on the ceiling side of the accelerator 2.

The front wall body 63 is disposed so as to cover the front face side of the accelerator 2. The front wall body 63 is formed, for example, so as to cover the whole of the front face of the accelerator 2, halves on the front face side of both side portions of the accelerator 2, and half on the front face side of the surface on the ceiling side of the accelerator 2. The rear wall body 62 and the front wall body 63 may be wall bodies which are disposed to face each other with the accelerator 2 interposed therebetween and surround the accelerator 2, the targets 3, and the like to shield radiation.

The rear wall body 62 functions as a fixed-side radiation shielding wall body fixed to a floor surface, and the front wall body 63 functions as a movable-side radiation shielding wall body movable on the floor surface. The movable-side radiation shielding wall body is configured to be movable so as to approach and separate from the fixed-side radiation shielding wall body. In addition, it is acceptable if at least one of the rear wall body 62 and the front wall body 63 is configured to be movable, and the two may also be configured to he movable. The built-in shield 6 may also be configured to be provided with other radiation shielding wall bodies different from the rear wall body 62 and the front wall body 63. A movement mechanism or the like by a rail and a roller can be used for the movement of the front wall body 63.

The radiation shielding wall body constituting the built-in shield 6 is mainly formed by concrete. Specifically, the inside of a metallic frame bode is filled with concrete. As the concrete which is used, concrete having large specific gravity from the viewpoint of radiation shielding ability, for example, high-density concrete for shielding using an aggregate having large specific gravity, such as magnetic iron steel, can be suitably used Further, a configuration is also acceptable in which another radiation shielding material such as lead or polyethylene is provided on the inner surface side of the concrete.

Target Shield

Here, the RI manufacturing apparatus 1 according to this embodiment is provided with target shields 7 and 8 which may be wall bodies that are disposed between the built-in shield 6 and the accelerator 2 and surround the targets 3 to shield radiation. The target shield 7 is formed so as to cover the target 3A (3) disposed at a left side portion and shields radiation from the target 3A. The target shield 8 is formed so as to cover the target 3B (3) disposed at a right side portion and shields radiation from the target 3B. As the radiation from the targets 3A and 3B, neutron radiation and gamma rays, which result from nuclear reaction during operation, are present, and gamma rays which are generated from the activated targets 3A and 3B itself after shutdown are present.

The target shield 7 is provided with a front plate 71 covering the front face side of the target 3A, a side plate 72 covering the side face side of the target 3A, a back plate 73 covering the back face side of the target 3A, a top plate 74 covering the top face side of the target 3A, and a bottom plate 75 covering the bottom face side of the target 3A. The front plate 71 and the back plate 73 are disposed to face each other in the Y direction of the illustration with the target 3A interposed therebetween. Further, the front plate 71 is inclined in such a manner that an outer end portion is disposed further to the back than an inner end portion (an end portion on the accelerator 2 side), as shown in FIG. 1. The side plate 72 is disposed to face the accelerator 2 with the target 3A interposed therebetween. The top plate 74 and the bottom plate 75 are disposed to face each other in the Z direction of the illustration with the target 3A interposed therebetween.

The target shield 8 is provided with a front plate 81 covering the front face side of the target 3B, a side plate 82 covering the side face side of the target 3B, a back plate 83 covering the back face side of the target 3B, and a top plate 89 covering the top face side of the target 3B. The front plate 81 and the back plate 83 are disposed to face each other in the Y direction of the illustration with the target 3B interposed therebetween. Further, the front plate 81 is inclined in such a manner that an outer end portion is disposed further to the back than an inner end portion (an end portion on the accelerator 2 side), as shown in FIG. 1. The side plate 82 is disposed to face the accelerator 2 with the target 3B interposed therebetween.

In the target shield 8, a radiation shielding wall body is not disposed on the bottom face side. Further, in the target shield 8, as shown in FIG. 1, the back plate 83 is disposed on the back face side of the vacuum pump 4 disposed on the back surface of the target 38. The vacuum pump 4 is disposed in a space surrounded by the target shield 8. However, the back plate 83 may also be disposed between the target 3B and the vacuum pump 4. Further, in a case where components other than the target 3 is disposed in the space surrounded by the target shield 8, a configuration is also acceptable in which a radiation shielding wall body is disposed only at a portion corresponding to the target 3 in the up-and-down direction Z. The side plate 82 of the target shield 8 may also be configured to be divided into a plurality (in this embodiment, two) in the front-and-back direction Y.

In addition, the shape and disposition of the target shield are not limited to those described above, and other target shields are also acceptable, and in short, it is also acceptable if the target shield has a configuration in which it is disposed so as to surround the target 3 (3A or 313) and can shield radiation which is generated from the target 3. For example, a configuration is also acceptable in which the target shield is not provided with the top plate 71 or 81 and/or the bottom plate 75. A target shield which may be a wall body that shields radiation advancing to a plane intersecting the horizontal plane (the X-Y plane) is also acceptable.

Target Shield: Double Structure

Figure 5:
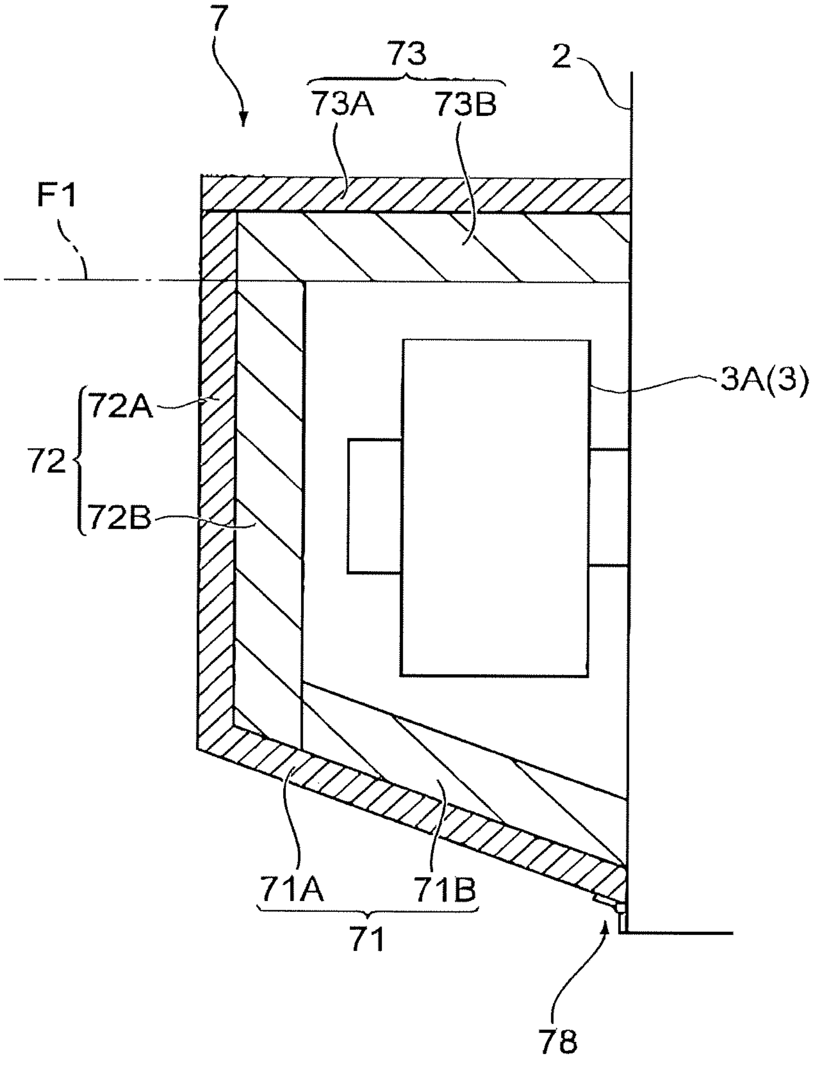
FIG. 5 is an enlarged cross-sectional view showing the target shield (on the left) of the RI manufacturing apparatus according to the embodiment of the present invention.

FIG. 5 an enlarged cross-sectional view showing the target shield 7. The target shield 7 is provided with gamma ray shielding plates 71A, 72A, and 73A which shield gamma rays, and neutron radiation shielding plates 71B, 72B, and 73B, each of which is disposed on the target 3 side of each gamma ray shielding plate and shields neutron radiation, as shown in FIG. 5. The front plate 71 has a configuration in which the gamma ray shielding plate 71A disposed outside in a plate thickness direction and the neutron radiation shielding plate 71B disposed inside are laminated. The side plate 72 has a configuration in which the gamma ray shielding plate 72A disposed outside in a plate thickness direction and the neutron radiation shielding plate 72B disposed inside are laminated. The back plate 73 has a configuration in which the gamma ray shielding plate 73A disposed outside in a plate thickness direction and the neutron radiation shielding plate 73B disposed inside are laminated. Similarly, each of the top plate 74 and the bottom plate 75 also has a configuration in which a gamma ray shielding plate and a neutron radiation shielding plate are laminated.

Figure 6:
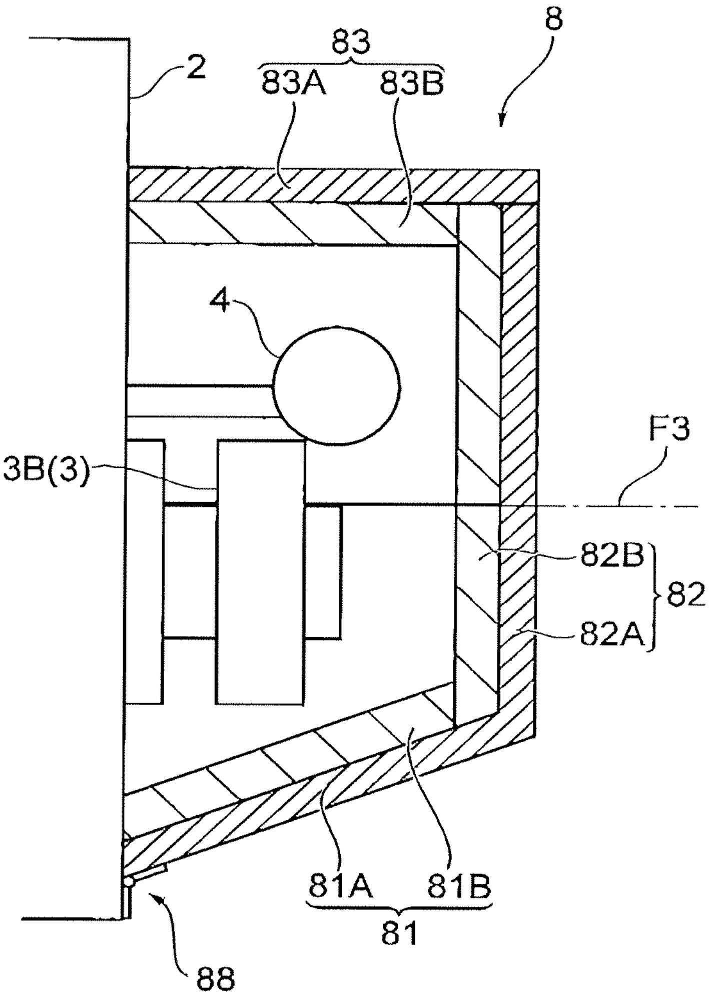
FIG. 6 is an enlarged cross-sectional view showing the target shield (on the right) of the RI manufacturing apparatus according to the embodiment of the present invention.

FIG. 6 an enlarged cross-sectional view showing the target shield 8. The target shield 8 is provided with gamma ray shielding plates 81A, 82A, and 83A which shield gamma rays, and neutron radiation shielding plates 81B, 82B, and 83B, each of which is disposed on the target 3 side of each gamma ray shielding plate and shields neutron radiation, as shown in FIG. 6. The front plate 81 has a configuration in which the gamma ray shielding plate 81A disposed outside in a plate thickness direction and the neutron radiation shielding plate 81B disposed inside are laminated. The side plate 82 has a configuration in which the gamma ray shielding plate 82A disposed outside in a plate thickness direction and the neutron radiation shielding plate 82B disposed inside are laminated. The back plate 83 has a configuration in which the gamma ray shielding plate 83A disposed outside in a plate thickness direction and the neutron radiation shielding plate 83B disposed inside are laminated. Similarly, the top plate 84 also has a configuration in which a gamma ray shielding plate and a neutron radiation shielding plate are laminated.

Each neutron radiation shielding plate is fixed to the inner side (the surface on the target 3 side) of each gamma ray shielding plate by using a bolt and a nut, for example. As a radiation shielding material which shields a neutron radiation, polyethylene (PE), water ($H_2O$), or the like can be given. As a radiation shielding material which shields a gamma ray, lead (Pb), tungsten (W), or the like can be given. Further as the radiation shielding material which shields a gamma ray, substance having density equal to or greater than that of iron (Fe) is also acceptable. As the radiation shielding material, other materials may also be used.

Target Shield; Door

FIG. 3 is a diagram showing a state where doors of the target shields have been opened. As shown in FIG. 3, the target shields 7 and 8 are configured to have openable and closable doors 7D and 8D. In the target shield 7, the front plate 71, the side plate 72, the top plate 74, and the bottom plate 75 are formed in an integrated fashion, thereby functioning as the openable and closable door 7D. In the target shield 8, the front plate 81, the side plate 82, and the top plate 84 are formed in an integrated fashion, thereby functioning as the openable and closable door OD.

The door 7D of the target shield 7 has a hinge 78, thereby being configured to be able to oscillate around the central shaft extending in the Z-axis direction. The door 8D of the target shield 8 has a hinge 88, thereby being configured to be able to oscillate around the central shaft extending in the Z-axis direction. Further, the configurations of the doors 7D and 8D are not limited to the configurations of being provided with the hinges 78 and 88, and for example, a configuration is also acceptable in which a portion of the wall body of each of the target shields 7 and 8 slides, thereby being opened and closed.

Further, as shown in FIG. 1, a configuration is made such that in a state where the door 7D has been closed, a joint (a joint surface) F1 between the door 7D of the target shield 7 and the back plate 73 is formed at a position deviated from a joint F2 between the parts (the rear wall body 62 and the front wall body 63) of the built-in shield 6, thereby not being disposed on the same straight line as the joint F2. Similarly, a configuration is made such that in a state where the door 8D has been closed, a joint F3 between the door 8D of the target shield 8 and another member is formed at a position deviated from a joint F4 between the parts of the built-in shield 6, thereby not being disposed on the same straight line as the joint F4.

Target Shield: Cutout Portion

Further, in the target shield 7, a cutout portion 75*a*, through which a lead-out tube for extracting the manufactured RIs from the target 3 passes, is formed. The cutout portion 75*a* is preferably provided on the lower surface side of the target shield 7. In the target shield 7 according to this embodiment, the cutout portion 75*a* is provided in the bottom plate 75 and the lead-out tube is led out of the target shield 7 through the cutout portion 75*a*. The lead-out tube passes the inside of a pit provided on the floor surface and gets out of the RI manufacturing apparatus.

Operation

Next, an operation of the RI manufacturing apparatus 1 configured in this manner will be described. First, a charged particle is accelerated by the accelerator 2, so that the targets 3 are irradiated with a charged particle beam. Target water in the accommodating portion of each target 3 is irradiated with the charged particle beam and causes a nuclear reaction, thereby manufacturing a RI. The manufactured RI flows in the lead-out tube and is sent to the outside of the RI manufacturing apparatus 1. For example, the manufactured RI is supplied to a radioactive compound synthesis device (an RI compound synthesis device) for synthesizing an RI compound. The RI compound synthesized in the RI compound synthesis device is supplied to and concentrated in a radioactive drug concentrating device and recovered as a radioactive drug (a product).

Further, during operation, the built-in shield 6 and the target shields 7 and 8 are used i closed states. In the operation of the RI manufacturing apparatus 1, radiation generated in the targets 3 is shielded by the target shields 7 and 8 and also shielded by the built-in shield 6.

Subsequently, in a case where maintenance of the RI manufacturing apparatus 1 is carried out in a shutdown state, the front wall body 63 of the built-in shield 6 is moved, thereby opening the inside. At this time, since the target shields 7 and 8 are in the closed states, even in a case where the targets 3 have been activated, the radiation which is generated from the targets 3 is shielded by the target shields 7 and 8. In this way, in the case of maintaining equipment other than the target 3, it is possible to start maintenance work without waiting for attenuation of the radiation from the target 3. For this reason, since there is no need to wait for attenuation of the radiation from the target 3, as in the past, it is possible to shorten a shutdown time for maintenance work.

In this manner, in the RI manufacturing apparatus 1 according to this embodiment, since the RI manufacturing apparatus 1 is provided with the target shields 7 and 8 which surround the targets 3 to shield radiation, it is possible to shield radiation which is radiated from the activated targets 3. For this reason, it is possible to reduce the fear of exposure of a worker. Further, because of a configuration in which the target shields 7 and 8 are provided further to the inside than the built-in shield 6, the built-in shield 6 disposed further to the outside than the target shields 7 and 8 produces the same shielding effects as in the past by using a smaller amount of shielding material than in the past, so that it is possible to reduce the amount of shielding material used.

Further, since in each of the target shields 7 and B, the neutron radiation shielding plate is provided on the inner side (on the target 3 side) of the gamma ray shielding plate, it is possible to shield the gamma rays which are generated by hitting of neutron radiation from the target 3 against the neutron radiation shielding plate, by the outer gamma ray shielding plate.

Further, since each of the target shields 7 and 8 is configured to have a door, during maintenance of the target 3, it is possible to easily access the target 3 by opening the door. Further, since a configuration is made such that the joint between each of the target shields 7 and 8 and an adjacent member and the joint between the parts of the built-in shield 6 are not disposed on the same straight line, it is possible to reduce the fear of transmission of radiation through a joint between radiation shielding walls.

Further, the cutout portion 75*a* is provided in the bottom plate 75 of the target shield and the cutout portion 75*a* is used as an opening portion which passes the lead-out tube therethrough In this manner, if the cutout portion which passes the lead-out tube therethrough is provided on the bottom face side of the target 3, the radiation passed the cutout portion is attenuated by being hit on and reflected by the floor surface (for example, concrete or the like). Further, attenuation due to the distance of the radiation also increases due to reflection of the radiation. For this reason, it is possible to reduce the fear of exposure of a worker. Further, since there is also no need for a worker to enter beneath the target shields 7 and 8 during maintenance, the fear of exposure by the radiation advancing downward is small.

Although the present invention has been specifically described above on the basis of the embodiment thereof, the present invention is not limited to the above-described embodiment. For example, in the above-described embodiment, the target shield is configured to have the gamma ray shielding plate and the neutron radiation shielding plate. However, a target shield formed by the gamma ray shielding plate is also acceptable.

Further, in the above-described embodiment, the cutout portion which passes the lead-out tube therethrough is formed in the bottom plate. However, the position of the cutout portion is not limited to the bottom plate. A configuration is also acceptable in which an opening which passes the lead-out tube or the like therethrough is provided in the back plate, the top plate, or the like.

Further, the target shield is not limited to a configuration in which it is fixed to the accelerator side, and for example, a target shield fixed to the rear wall body 62 which does not move or a target shield fixed to the floor surface through a support member is also acceptable.

Further, in the above-described embodiment, the accelerator has been described as being a cyclotron. However, the accelerator is not limited to the cyclotron and another accelerator (for example, a synchro-cyclotron or a synchrotron) is also acceptable.

It should be understood that the invention is not limited to the above-described embodiment, but may be modified into various forms on the basis of the spirit of the invention. Additionally, the modifications are included in the scope of the invention.

What is claimed is:

1. A Radioactive Isotope (RI) manufacturing apparatus comprising:

an accelerator which accelerates charged particles;

a target which is irradiated with the charged particle accelerated by the accelerator, thereby manufacturing a radioactive isotope;

a built-in shield that is a wall body which is configured to be provided inside a building and surrounds the accelerator and the target to shield radiation; and a target shield that is a wall body which is disposed in an internal space formed so as to be surrounded by the built-in shield and surrounds the target to shield the radiation; wherein, said target shield is connected to the lead-out tube at the bottom of the shield in order to further attenuate radiation.

2. The RI manufacturing apparatus according to claim 1, wherein the target shield includes a gamma ray shielding plate which shields gamma rays, and a neutron radiation shielding plate which is disposed on the target side of the gamma ray shielding plate and shields neutron radiation.

3. The RI manufacturing apparatus according to claim 1, wherein the built-in shield is composed of a plurality of parts and at least one of the plural parts is movable, the target shield includes an openable and closable door, and a joint between the door and another member adjacent to the door is formed at a position deviated from a joint between the plural parts of the built-in shield.

4. The RI manufacturing apparatus according to claim 1, wherein a cutout portion which makes a lead-out tube that leads out the radioactive isotopes in the target pass therethrough is provided on the lower surface side of the target shield.

* * * * *